US008557831B2

(12) United States Patent
Johnson et al.

(10) Patent No.: US 8,557,831 B2
(45) Date of Patent: Oct. 15, 2013

(54) COMPOSITIONS AND METHODS FOR TREATMENT AND PREVENTION OF INSULIN RESISTANCE

(75) Inventors: Richard J. Johnson, Gainesville, FL (US); Takahiko Nakagawa, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1141 days.

(21) Appl. No.: 11/572,270

(22) PCT Filed: Jul. 21, 2005

(86) PCT No.: PCT/US2005/025910
§ 371 (c)(1),
(2), (4) Date: Jan. 18, 2007

(87) PCT Pub. No.: WO2006/012438
PCT Pub. Date: Feb. 2, 2006

(65) Prior Publication Data
US 2008/0096904 A1    Apr. 24, 2008

Related U.S. Application Data

(60) Provisional application No. 60/589,921, filed on Jul. 21, 2004.

(51) Int. Cl.
*A01N 43/90*        (2006.01)
(52) U.S. Cl.
USPC ...................................................... 514/263.3
(58) Field of Classification Search
USPC ...................................................... 514/263.3
See application file for complete search history.

(56) References Cited

U.S. PATENT DOCUMENTS

| 6,162,831 A * | 12/2000 | Kelly et al. ............ 514/646 |
| 6,353,009 B1 * | 3/2002 | Fujiwara et al. ........ 514/365 |
| 6,589,573 B2 | 7/2003 | Unno et al. |
| 2002/0019360 A1 * | 2/2002 | Kivlighn et al. ........ 514/44 |
| 2005/0090472 A1 * | 4/2005 | Yoshida et al. ......... 514/81 |

FOREIGN PATENT DOCUMENTS

| WO | WO02/00210 | 1/2002 |
| WO | WO 03/042185 | * 5/2003 |

OTHER PUBLICATIONS

Marino, Understanding Insulin Resistance Key to Diabetes Prevention. Reporter, Vanderbilt Medical Center. (Accessed May 4, 2009 at http://www.mc.vanderbilt.edu/reporter/index.html?ID=7209.).*
Milionis, Management of Hypertension and Dyslipidaemia in Patient Presenting with Hyperuricaemia: Case Histories, Current Medical Research and Opinion vol. 16, No. 3, pp. 164-170, 2000.*
Kacmaz (Enzymatic antioxidant defence mechanism in rat intestinal tissue is changes after ischemia-reperfusion, Effects of an allopurinol plus antioxidant combination, Canadian Journal of Surgery, Dec. 1, 1999—accessed from http://www.highbeam.com/doc/1P3-47162655.html on Dec. 12, 2012).*
Nakagawa, A causal role for uric acid in fructose-induced metabolic syndrome, Am J Physiol Renal Physiol 290: F625-F631, 2006.*
"322 Elevated serum uric acid levels in pregnancy induced hypertension (PIH) are correlated to insulin resistance" American Journal of Obstetrics & Gynecology, MOSBY, St. Louis, MO, US LNKD-DOI: 10: 1016/S0002-9378(01)80353-7, vol. 185, No. 6 Dec. 1, 2001, p. S170, XP005471655 ISSN: 002-9378.
Diet and Medication in the Treatment of Hyperuricemia in Hypertensive Patients, Maria do Rosario Gondim Peixoto et al., Arq. Bras Cardiol, vol. 76, No. 6, 468-72, 2001i.
Allopurinol Normalizes Endothelial Dysfunction in Type 2 Diabetics with Mild Hypertension, Robert Butler et al., Hypertension, 2000, vol. 35, No. 3, p. 746-51i.

* cited by examiner

*Primary Examiner* — Frederick Krass
*Assistant Examiner* — Adam C Milligan
(74) *Attorney, Agent, or Firm* — Timothy H. Van Dyke; Beusse, Wolter, Sanks, Mora & Maire, P.A.

(57) ABSTRACT

Disclosed herein are methods of delaying the onset or treating diabetes that comprises administering a uric acid lowering agent. The inventors have made the remarkable discovery that elevated uric acid levels are not a corollary to insulin resistance, but rather a primary mediator of insulin resistance. Specifically exemplified are methods that involve administering to a patient susceptible to development of diabetes a composition comprising a uric acid lowering agent in a regimen that maintains serum uric acid levels below at least 5.2 to 5.5 mg/dl.

21 Claims, 1 Drawing Sheet

COMPOSITIONS AND METHODS FOR TREATMENT AND PREVENTION OF INSULIN RESISTANCE

CROSS-REFERENCE TO RELATED APPLICATIONS

This application claims benefit of the Jul. 21, 2004, filing date of U.S. provisional patent application No. 60/589,921.

BACKGROUND OF THE INVENTION

Diabetes mellitus is characterized by a broad array of physiologic and anatomic abnormalities, for example, altered glucose disposition, hypertension, retinopathy, abnormal platelet activity, aberrations involving large, medium and small sized vessels, and other problems encountered in diabetic patients. Diabetes is classified into two categories: primary and secondary. Primary diabetes includes: 1) Insulin-dependent diabetes mellitus (IDDM, Type 1), 2) Non-insulin-dependent diabetes mellitus (NIDDM, Type 2) including a) Nonobese NIDDM, b) Obese NIDDM and c) Maturity-onset diabetes of the young. Primary diabetes implies that no associated disease is present, while in the secondary diabetes some other identifiable condition causes or allows a diabetic syndrome to develop, for example, 1) Pancreatic disease, 2) Hormonal abnormalities, 3) Drug or chemical induced, 4) Insulin receptor abnormalities, 5) Genetic syndromes and 6) Others.

Insulin dependence in this classification is not equivalent to insulin therapy, but means that the patient is at risk for ketoacidosis in the absence of insulin. It has been suggested that the terms insulin-dependent and non-insulin-dependent describe physiologic states (ketoacidosis-prone and ketoacidosis-resistant, respectively), while the terms Type 1 and Type 2 refer to pathogenetic mechanisms (immune-mediated and non-immune-mediated, respectively). Using this classification, three major forms of primary diabetes are recognized: (1) type 1 insulin-dependent diabetes, (2) type 1 non-insulin-dependent diabetes, and (3) type 2 non-insulin-dependent diabetes.

Secondary forms of diabetes encompass a host of conditions such as pancreatic disease, hormonal abnormalities, genetic syndromes, and others.

Insulin-dependent diabetes mellitus often develops in childhood or adolescence while the onset of NIDDM generally occurs in middle or late life. Patients with NIDDM are usually overweight and constitute 90 to 95 percent of all diabetics. IDDM results from the destruction of beta cells by an autoimmune process that may be precipitated by a viral infection. NIDDM is characterized by a gradual decline in beta cell function and varying degrees of peripheral resistance to insulin. The annual incidence of IDDM ranges from 10 cases per 100,000 persons for nonwhite males to 16 cases per 100,000 persons for white males. LaPorte, R. E. et al., 1981, Diabetes 30: 279. The prevalence of NIDDM increases with age, especially after age 45 and is higher among blacks than whites and certain populations such as Asian Indians living in South Africa and England. Malter, H. M. et al., 1985, Br. Med. J. 291: 1081. Gestational diabetes occurs in 2.4 percent of all pregnancies in the United States annually. Freinkel, N. et al., 1985, N. Engl. J. Med. 313: 96. Pregnancy is also a state of insulin resistance. This insulin resistance is exacerbated in gestational diabetes which may predispose patients to the various hypertensive syndromes of pregnancy associated with Type 2 NIDDM. Bardicef, M. et al., 1995, Am. J. Gynecol. 172: 1009-1013.

Current therapies for IDDM include insulin therapy, and for NIDDM will include dietary modification in a patient who is overweight and hypoglycemic agents, e.g., tolbutamide, chlorpropamide, acetohexamide, tolazamide, glipizide and glyburide, all of which act by stimulating the release of insulin from the beta cells.

Insulin resistance and hyperuricemia are considered a part of the 'metabolic syndrome' or 'syndrome X' of obesity, insulin resistance, hypertriglyceridemia and hyperuricemia, which underlies the pathogenesis of type II diabetes. Insulin resistance is an impaired metabolic response to our body's own insulin so that active muscle cells cannot take up glucose as easily as they should. In that situation, the blood insulin levels are chronically higher which inhibits our fat cells from giving up their energy stores to let us lose weight. The condition can exist unrecognized and metabolic damage can occur before a full blown Type 2 diabetes is finally diagnosed. Insulin resistant diabetics are 2-5 times more likely to die from heart attack or stroke than are non diabetics. Currently metabolic syndrome is epidemic both in the United States and throughout the world, resulting in exponential increases in health care cost and causing great morbidity and mortality due to the increased risk for cardiovascular and renal disease in this population. Most studies suggest that the epidemic is due to the adaptation of 'Westernized diet'—this diet is also known to increase our risk for gout (Johnson R J, Rideout B: Uric acid and diet: insights into the Epidemic of Cardiovascular Disease. N Engl J Med (editorial) 2004; 350:1071-1074).

It has widely been assumed that the rise in serum uric acid associated with insulin resistance is due to the effect of insulin to increase urate reabsorption in the renal tubule, and hence it had been assumed that the hyperuricemia associated with insulin resistance does not have a causal role in the syndrome.

SUMMARY OF THE INVENTION

The inventors have made the remarkable discovery that elevated levels of uric acid is a primary mediator of insulin resistance. The subject invention provides a new approach to preventing and/or treating the insulin resistance and diabetes.

In a specific embodiment, the subject invention pertains to methods of administering a uric acid lowering agent (UALA) to a patient susceptible to developing insulin resistance or suffering from insulin resistance. As part of the medical treatment, serum samples are typically obtained and tested so that serum uric acid levels may be monitored in conjunction with the administration of the UALA.

DETAILED DESCRIPTION OF THE INVENTION

Figure 1:
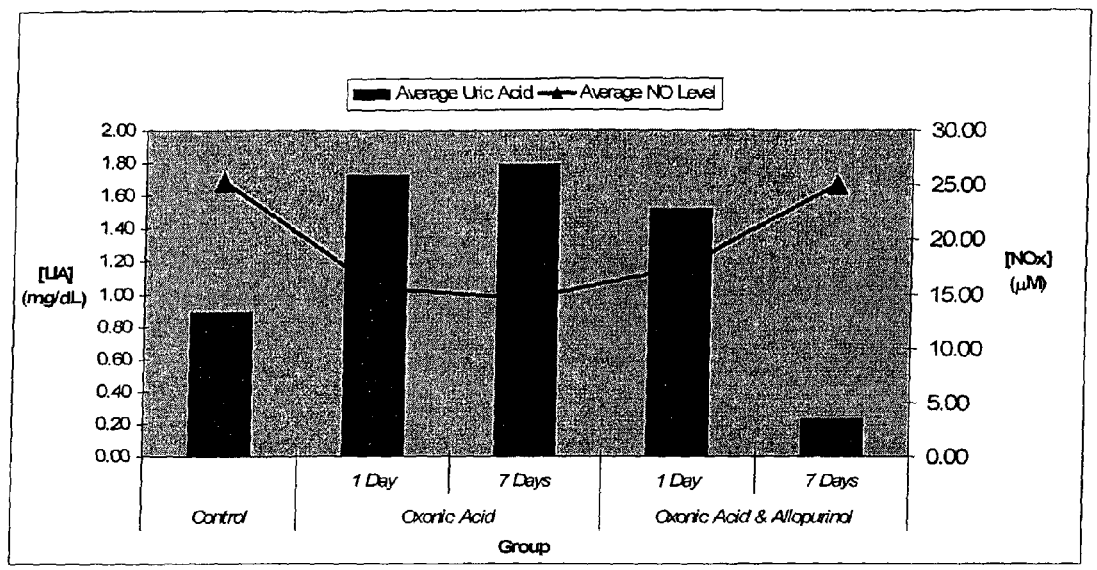
FIG. 1 is a graph showing the relationship of serum uric acid and serum nitrites at 1 and 7 Days of hyperuricemic induced rats. Serum was analyzed for uric acid concentration and nitrites/nitrates ($NO_x$) by chemiluminescence method.

The pharmaceutical compositions provided herein contain therapeutically effective amounts of one or more agents to lower uric acid that are useful in the treatment or prevention of insulin resistance. The inventors have discovered that hyperuricemia plays a critical role in causing insulin resistance.

The term "uric acid lowering agent" or UALA refers to substances known to lower serum uric acid levels in mammals. Typically, the UALA may limit serum uric acid levels by at least about 0.2 mg/dl. UALAs include, but are not limited to, xanthine oxidase inhibitors such as allopurinol, hydroxyakalone, TEI-6720, carprofen, febuxostat, and y-700; uricosurics such as benziodarone, benzbromarone, probenecid; uricase derivatives such as Rasburicase and Pegylated uricase; gene based therapies such as uricase overexpression or blockade of URAT-1; a supplement of the uricase protein which might be delivered as a conjugate with polyethylene glycol or another delivery system; and a urate channel inhibitor.

The compounds are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that reduces serum uric acid levels at least 0.5 mg/dl to be equal to or less than 5.5 mg/dl. In a most preferred embodiment, effective amount is such as to lower serum uric acid levels to less than or equal to 5.5 mg/dl and more than or equal to 4.0 mg/dl. Preferably still, the effective amount is such as to lower serum uric acid levels to less than or equal to 5.2 mg/dl and more than or equal to 4.5 mg/dl. It is known that uric acid acts as antioxidant in the body. Epidemiological studies performed by the inventor have uncovered that the positive effects of avoiding insulin resistance are achieved by lowering serum uric acid levels to at least 5.5 mg/dl. However, the positive effects are largely negated as serum uric acid levels fall below 4.0 mg/dl. At levels below 4.0 mg/dl, the loss of antioxidant activity of uric acid may actually predispose to an increased incidence of cardiovascular disease and mortality. The UALA may be administered concomitantly or sequentially with one or more known antioxidants, such as, but not limited to, vitamin C, alpha-lipoic acid, Vitamin E, beta carotene, selenium, zinc, carnosine, green tea, soy and isoflavones, tempol, etc. Such combination may be beneficial regardless of uric acid levels, but may be particularly helpful if dosages of UALA are administered that lower the uric acid below 4.5 mg/dl.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

The term "average serum uric acid level(s)" as used herein refers to an average of two or more uric acid readings obtained from a patient. The two or more uric acid readings may be taken within hours of each other. Preferably, the two or more readings are obtained at least a week from each other.

The term "regimen" as used herein refers to an administration of two or more dosages sequentially spaced in time so as to maintain average serum uric acid levels at a predetermined level. The space in time is preferably 3 or more hours.

In addition, the compounds may be formulated as the sole pharmaceutically active ingredient in the composition or may be combined with other active ingredients. Liposomal suspensions, including tissue-targeted liposomes, particularly tumor-targeted liposomes, may also be suitable as pharmaceutically acceptable carriers. These may be prepared according to methods known to those skilled in the art. For example, liposome formulations may be prepared as described in U.S. Pat. No. 4,522,811.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems (see, e.g., Rosenthal et al. (1996) Antimicrob. Agents Chemother. 40(7):1600-1603; Dominguez et al. (1997) J. Med. Chem. 40:2726-2732; Clark et al. (1994) Molec. Biochem. Parasitol. 17:129; Ring et al. (1993) Proc. Natl. Acad. Sci. USA 90:3583-3587; Engel et al. (1998) J. Exp. Med. 188(4):725-734; Li et al. (1995) J. Med. Chem. 38:5031) and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to lower uric acid concentrations at least 0.5 mg/dl to achieve 5.5 mg/dl or lower serum uric acid levels.

Typically a therapeutically effective dosage should produce a serum concentration of active ingredient of from about 0.1 ng/ml to about 50-100 µg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Preferred pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for reducing uric acid at or below 5.5 mg/dl. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, rectally, topically and locally. For oral administration, capsules and tablets are presently preferred. The compositions are in liquid, semi-liquid or solid form and are formulated in a manner suitable for each route of administration. Preferred modes of administration include parenteral and oral modes of administration. Oral administration is presently most preferred.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active ingredient, preferably 0.1-85%, typically 75-95%.

The active compounds or pharmaceutically acceptable derivatives may be prepared with carriers that protect the compound against rapid elimination from the body, such as time release formulations or coatings.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles, and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound of formula I in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, preferably 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as transdermal patches and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theorem oil), glycerin-gelatin, carbora (polyoxyethylene glycol) and appropriate mixtures of mono-, did- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Articles of Manufacture

The compounds or pharmaceutically acceptable derivatives may be packaged as articles of manufacture containing packaging material, a compound or pharmaceutically acceptable derivative thereof provided herein, which is effective for reducing serum uric levels.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,352. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated for treatment and prevention of insulin resistance.

It has recently been reported that raised uric acid levels do not impair endothelial function in humans. Waring et al., *Heart* 2004, 90:155-159. The inventors believe that this report does not fully reveal the effects of raised uric acid levels in the blood. Waring et al reported that the infusion of uric acid into the forearm vein of humans does not impair endothelial function as measured by brachial artery reactivity. However, the authors examined the effect immediately after infusion of uric acid, and it remains possible that the effect on NO production is delayed. Indeed, with experimental hyperuricemia, hypertension does not develop until several weeks after the uric acid is raised. It is also possible that allopurinol may improve NO production in subjects by a different mechanism, such as lowering xanthine oxidase-induced oxidants. Contrary to the Waring et al. report, the inventors believe that uric acid does indeed impair endothelial dysfunction and as a result NO production is impaired.

Example 1

Hyperuricemia Induces Endothelial Dysfunction by Inhibiting the Production of NO in Rats Methods Male Sprague-Dawley rats were housed in standard conditions and fed normal diets. Hyperuricemia was induced with an uricase inhibitor, oxonic acid (OA; 750 mg/kg/day), by gavage, with control rats receiving vehicle. Allopurinol (AP) was used to block hyperuricemia by placing AP in the drinking water (150 mg/L). Rats were divided into four groups: (1) Control, (2) AP only, (3) OA only, and (4) OA+AP. Systolic blood pressure was measured using a tail-cuff sphygmomanometer. The amount of drinking water consumed and changes in body weight were noted. Rats were sacrificed at one and seven days. Serum was analyzed for uric acid concentration and nitrites/nitrates ($NO_x$) by chemiluminescence method. (Prabhakar S S: Inhibition of mesangial iNOS by reduced extracellular pH is associated with uncoupling of NADPH oxidation. *Kidney Int* 61:2015-2024, 2002). Statistical analysis between subgroups was performed using ANOVA.

Results

Figure 2:
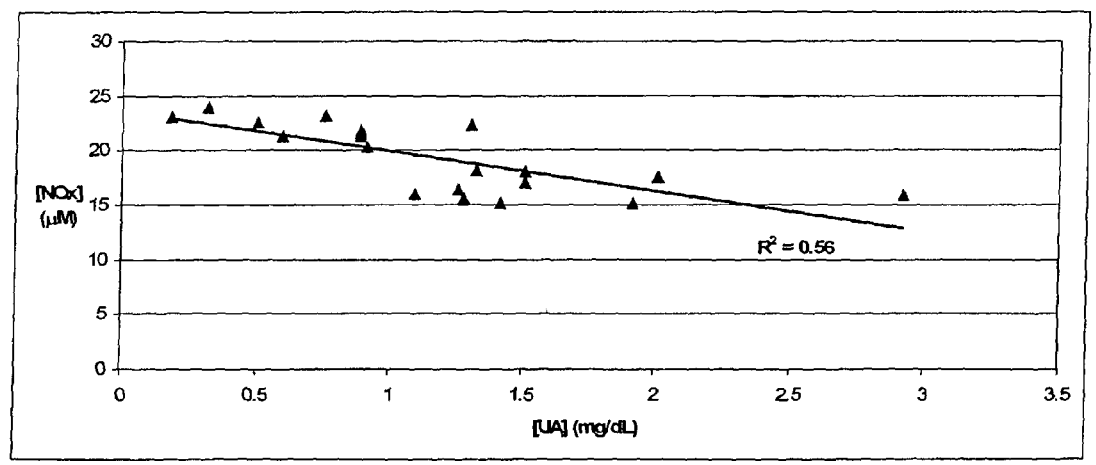
FIG. 2 represents a graph that shows the linear correlation of serum uric acid and serum nitrites.

There was no difference in the amount of water consumed and the change in body weight between the three groups over seven days. OA induced a mild hyperuricemia at both 1 day (1.7±0.7 vs. 0.8±0.4 mg/dL in OA vs. Control, p<0.05) and 7 days (1.8±0.4 vs. 0.9±0.7 mg/dL in OA vs. Control, p<0.05). AP only had a mild and non-significant effect on serum uric acid concentrations at day 1 (1.52±0.3 mg/dL, p=NS), but effectively reversed the hyperuricemia at 7 days (0.3±0.2 mg/dL, p<0.001). Serum nitrites and nitrates ($NO_x$) were reduced by 40-50% in hyperuricemic rats at both 1 day (15.6±0.4 vs. 22.6±1.0 μmol/L in OA vs. Control, p<0.001) and 7 days (14.6±1.1 vs. 27.5±1.3 μmol/L in OA vs. Control, p<0.001). This decrease in $NO_x$ was improved slightly by AP at 1 day (17.4±0.8 μmol/L, p<0.001) and reversed completely at 7 days (25.0±0.8 μmol/L, p<0.001). (FIG. 1.) There was also a direct linear correlation between serum UA and $NO_x$ (FIG. 2). Rats treated with AP alone did not show a significant change in either serum UA or $NO_x$ concentration. Rats treated with OA also showed a trend toward higher systolic blood pressure at 7 days (178±18 vs. 158±16 vs. 147±11 mm Hg in OA vs. Control vs. OA/AP, p=NS).

Conclusions

Most mammals have the enzyme uricase that degrades uric acid to allantoin with the generation of oxidants. In humans, uricase is mutated resulting in higher uric acid levels. Rats administered an uricase inhibitor (oxonic acid) develop mild hyperuricemia, hypertension, and vascular disease that is mediated by activation of the renin-angiotensin system, a loss of macula densa NO synthase, and the development of microvascular disease (Mazzali M, Hughes J, Kim Y G, Jefferson J A, Kang D H, Gordon K L, Lan H Y, Kivlighn S, Johnson R J: Elevated uric acid increases blood pressure in the rat by a novel crystal-independent mechanism. *Hypertension* 38:1101-1106, 2001). In this study, it was demonstrated that hyperuricemic rats have a fall in serum nitrites (a reflection of NO production) that is reversed by allopurinol. Furthermore, there was a direct linear correlation between serum uric acid and serum nitric oxide. The induction of hyperuricemia also showed a trend towards increased systolic blood pressure. This data shows that hyperuricemia leads to endothelial dysfunction in the rat. As discussed briefly above, this is a contrary conclusion to that was earlier reported by Waring et al which concluded that the infusion of uric acid into humans does not impair endothelial function (Waring W S, Adwani S H, Breukels O, Webb D J, Maxwell S R: Hyperuricaemia does not impair cardiovascular function in healthy adults. *Heart* 90:155-159, 2004). However, these studies did not measure nitric oxide levels nor mention effects of sustained hyperuricemia on endothelial-dependent vasodilatation.

Without being held to any specific mechanism, the inventors believe that raised serum uric acid levels ultimately lead to insulin resistance mediated by impairment of endothelial function and inhibition of NO production. As support for this mechanistic theory, the inventors cite to Cook et al., *Swiss Med Wkly*, 2003, 133:360-363, which shows that knock-out mice harboring a genetic defect for endothelial nitric oxide synthase develop many of the abnormalities associated with the metabolic syndrome. Accordingly, it is the inventors' position that insulin resistance results from raised serum uric acid levels, likely caused by the high sugar, fructose-generating western diet, which results in endothelial dysfunction and inhibition of NO production, and ultimately to insulin resistance. Thus, controlling a person's average serum uric acid levels by administration of UALA will have the dramatic affect of delaying the onset of the characteristics of the metabolic syndrome, including insulin resistance.

According to another embodiment, the subject invention pertains to a method of determining the uric acid increasing load per mass of food. The method may comprise the administration of a quantity of a food item and determination of the affect of such administration on the uric acid levels of such food. Thus, one or more food items are tested and the information is used to generate a uric acid increasing index (or 'UA index'). WO-A 2005040752 and U.S. Patent Pub No. 2004043106 are incorporated by reference, which describes methodology for establishing glycemic loads of foods. The teachings of such publication may be easily adaptable to producing correlating types of information relating to Uric Acid generating loads of foods, including fluids.

What is claimed is:

1. A method of lowering uric acid levels in a patient suffering from insulin resistance comprising:
   administering to said patient a composition comprising a uric acid lowering agent according to a regimen effective to maintain said patient's average serum uric acid level at or below 5.5 mg/dl, wherein said uric acid lowering agent is a xanthine oxidase inhibitor, a uricosuric, a uricase, a peqylated uricase, a rasburicase, a urate channel inhibitor, or a URAT-1 blocker, wherein said administering treats said insulin resistance.

2. The method of claim 1, further comprising determining said patient's average serum uric acid prior to said administering.

3. The method of claim 1, wherein said composition is administered over the course of at least one week.

4. The method of claim 1, wherein said composition is administered over the course of at least 2 weeks.

5. The method of claim 1, wherein said composition is administered over the course of at least 4 weeks.

6. The method of claim 1, wherein said composition is administered according to a regimen to maintain the average serum uric acid level equal to or below 5.5 mg/dl for at least 2 weeks.

7. The method of claim 6, wherein regimen is designed to maintain the average serum uric acid level equal to or below 5.5 mg/dl for at least 4 weeks.

8. The method of claim 6, wherein regimen is designed to maintain the average serum uric acid level equal to or below 5.5 mg/dl for at least 8 weeks.

9. The method of claim 6, wherein regimen is designed to maintain the average serum uric acid level equal to or below 5.5 mg/dl for at least 24 weeks.

10. The method of claim 6, wherein regimen is designed to maintain the average serum uric acid level equal to or below 5.5 mg/dl for at least 2 years.

11. The method of claim 1, wherein said composition is administered according to a regimen to maintain average serum uric acid levels between 4.5 mg/dl to 5.5 mg/dl for at least 12 weeks.

12. The method of claim 11, wherein said composition is administered according to a regimen to maintain average serum uric acid levels between 4.5 mg/dl to 5.5 mg/dl for at least 1 year.

13. A method of lowering uric acid levels in a patient suffering from insulin resistance comprising: determining said patient's average serum uric acid level; and administering to said patient a composition comprising a uric acid lowering agent according to a regimen effective to maintain said patient's average serum uric acid level between 4.5 mg/dl and 5.5 mg/dl for at least 4 weeks, wherein said uric acid lowering agent is a xanthine oxidase inhibitor, a uricosuric, a uricase, a peqylated uricase, a rasburicase, a urate channel inhibitor, or a URAT-1 blocker, wherein said administering treats said insulin resistance.

14. The method of claim 13, wherein said administering occurs according to a regimen effective to maintain said patient's average serum uric acid level between 4.5 mg/dl and 5.5 mg/dl for at least 12 weeks.

15. The method of claim 13, wherein said administering occurs according to a regimen effective to maintain said patient's average serum uric acid level between about 4.5 mg/dl and 5.5 mg/dl for at least 36 weeks.

16. A method of lowering uric acid levels in a patient suffering from insulin resistance comprising administering to said patient a composition comprising a uric acid lowering agent according to a regimen effective to maintain said patient's average serum uric acid level between 4.5 mg/dl and 5.5 mg/dl for at least 2 weeks, wherein said uric acid lowering agent is a xanthine oxidase inhibitor, a uricosuric, a uricase, a pegylated uricase, a rasburicase, a urate channel inhibitor, or a URAT-1 blocker, wherein said administering treats said insulin resistance.

17. The method of claim 1, wherein said uric acid lowering agent is a xanthine oxidase inhibitor.

18. The method of claim 17, wherein said xanthine oxidase inhibitor is febuxostat.

19. The method of claim 1, wherein said uric acid lowering agent is benziodarone, benzbromarone or probenecid.

20. The method of claim 1, wherein said uric acid lowering agent is a urate channel inhibitor.

21. The method of claim 1, wherein said uric acid lowering agent is a URAT-1 blocker.

\* \* \* \* \*